US012740837B2

(12) United States Patent
Boulangé et al.

(10) Patent No.: US 12,740,837 B2
(45) Date of Patent: Sep. 22, 2026

(54) SYSTEM FOR ROTATIONALLY AND TRANSLATIONALLY DRIVING AN ELONGATE FLEXIBLE MEDICAL INSTRUMENT

(71) Applicant: ROBOCATH, Rouen (FR)

(72) Inventors: Marc Boulangé, La Gaillarde (FR); Philippe Bencteux, Saint Martin du Vivier (FR)

(73) Assignee: ROBOCATH, Rouen (FR)

( * ) Notice: Subject to any disclaimer, the term of this patent is extended or adjusted under 35 U.S.C. 154(b) by 154 days.

(21) Appl. No.: 18/859,734

(22) PCT Filed: Apr. 26, 2023

(86) PCT No.: PCT/EP2023/060910

§ 371 (c)(1),
(2) Date: Oct. 24, 2024

(87) PCT Pub. No.: WO2023/208992

PCT Pub. Date: Nov. 2, 2023

(65) Prior Publication Data

US 2026/0183068 A1 Jul. 2, 2026

(30) Foreign Application Priority Data

Apr. 26, 2022 (FR) ...................................... 2203874

(51) Int. Cl.
*A61B 34/30* (2016.01)

(52) U.S. Cl.
CPC ........ *A61B 34/30* (2016.02); *A61B 2034/301* (2016.02)

(58) Field of Classification Search
CPC .......................... A61B 2034/301; A61B 34/30
See application file for complete search history.

(56) References Cited

U.S. PATENT DOCUMENTS

| | | | |
|---|---|---|---|
| 2017/0189128 | A1 | 7/2017 | Auld |
| 2020/0230360 | A1 | 7/2020 | Yu et al. |
| 2020/0261172 | A1 | 8/2020 | Romo et al. |
| 2020/0352420 | A1 | 11/2020 | Graetzel et al. |

FOREIGN PATENT DOCUMENTS

| | | | | |
|---|---|---|---|---|
| CN | 104644270 A | 5/2015 | | |
| EP | 1442720 A1 | 8/2004 | | |
| WO | WO-2021011533 A1 * | 1/2021 | ...... A61M 25/09041 |

OTHER PUBLICATIONS

International Search Report issued on Aug. 30, 2023, in corresponding International Application No. PCT/EP2023/060910; 10 pages.

* cited by examiner

*Primary Examiner* — Scott Luan
(74) *Attorney, Agent, or Firm* — Maier & Maier, PLLC

(57) ABSTRACT

A drive system for driving an elongate and flexible medical instrument along a main elongation axis, the drive system including a first roller and a second roller intended to cooperate in order to drive the medical instrument translationally along its main elongation axis and to drive the medical instrument rotationally about its main elongation axis. The first roller is coupled to a first shaft and the second roller is coupled to a second shaft.

21 Claims, 7 Drawing Sheets

SYSTEM FOR ROTATIONALLY AND TRANSLATIONALLY DRIVING AN ELONGATE FLEXIBLE MEDICAL INSTRUMENT

FIELD

This invention relates to systems and methods for driving elongate flexible medical instruments, and to the associated robotic systems.

More particularly, the invention relates to a system for driving an elongate flexible instrument rotationally and translationally, and to the robot comprising such a drive system.

BACKGROUND

Inserting an elongate flexible medical instrument into a patient, for example inserting a catheter or a guide, is a relatively conventional medical procedure. Such a medical procedure is used, for example, for treating vascular diseases.

However, since this procedure is monitored under X-rays, the doctor and medical staff in charge of this procedure are exposed to significant radiation when they perform such an operation repeatedly.

In order to reduce the risks to medical personnel, it is known to automate such an insertion.

For example, known document EP1442720 describes a catheter manipulation robot. This document describes a drive system comprising a pair of rollers that drives a medical instrument translationally along the main elongation axis of said medical instrument and rotationally about said main elongation axis of said medical instrument (see FIGS. 5 and 6). The translational movement of the medical instrument is ensured by the rotation of the rollers, while the rotational movement of the medical instrument is ensured by a translational movement of the rollers in opposite directions.

Document CN104644270 is also known, which again describes a catheter manipulation robot with a pair of rollers, in which the translational movement of the medical instrument is ensured by rotation of the rollers, while the rotational movement of the medical instrument is ensured by a translational movement of the rollers in opposite directions. However, in the solution described in this document, the medical instrument is driven translationally by a driving force from only one of the rollers: the roller which is equipped with a direct current motor (DC 8 motor illustrated in FIG. 1 of document CN104644270).

Document WO202111533 is also known, which again describes a catheter manipulation robot with a pair of rollers, in which the translational movement of the medical instrument is ensured by rotation of the rollers, while the rotational movement of the medical instrument is ensured by translational movement of the rollers in opposite directions. (see FIGS. 22A-22X). Document WO202111533 describes two embodiments for rotationally driving the rollers. According to the first embodiment, the medical instrument is driven translationally by a driving force from only one of the rollers. In the second embodiment, the two rollers are in contact so that the roller connected to the motor drives the other roller by friction. However, such a transmission by friction runs the risk of slippage occurring between the rollers, in particular when the force required to drive the medical instrument increases, for example when the medical instrument must pass through a lesion.

However, none of the proposed solutions are satisfactory in terms of efficiency in driving the medical instrument, as well as simplicity and compactness of the drive system.

SUMMARY

The purpose of the present invention is to provide a catheter robot that at least partially overcomes the above disadvantages.

More particularly, the invention aims to provide a drive system for an elongate and flexible medical instrument in which the transmission of movement provided by its motors is as efficient as possible.

The invention also aims to provide a drive system where the structure is as simple and compact as possible.

According to a first object, the invention proposes a drive system for driving an elongate and flexible medical instrument along a main elongation axis, said drive system comprising a first roller and a second roller which are intended to cooperate in order to drive the medical instrument translationally along its main elongation axis, and to drive the medical instrument rotationally about its main elongation axis, the first roller being coupled to a first shaft and the second roller being coupled to a second shaft, characterized in that:

- the drive system comprises a first motor which is coupled to the first shaft, said first motor being configured to drive the first shaft and the first roller rotationally about a first axis that is collinear with the first shaft, the first shaft being coupled to the second shaft in order to transmit motion from the first motor to said second shaft and thus drive the second shaft and the second roller rotationally about a second axis that is collinear with the second shaft, the medical instrument being driven translationally by a driving force transmitted both by the rotation of the first roller and by the rotation of the second roller; and
  - the drive system comprises a second motor which is coupled to the first shaft, said second motor being configured to drive the first shaft and the first roller translationally along the first axis, the first shaft being coupled to the second shaft in order to transmit motion from the second motor to said second shaft and thus drive the second shaft and the second roller translationally along the second axis in the opposite direction relative to the first roller, the medical instrument being rotated by a driving force transmitted both by the translation of the first roller and by the translation of the second roller; or
  - the drive system comprises a second motor which is coupled to the second shaft, said second motor being configured to drive the second shaft and the second roller translationally along the second axis, the second shaft being coupled to the first shaft in order to transmit motion from the second motor to said first shaft and thus drive the first shaft and the first roller translationally along the first axis in the opposite direction relative to the second roller, the medical instrument being rotated by a driving force transmitted both by the translation of the first roller and by the translation of the second roller;
- wherein the first shaft comprises a first gear which is meshed with an output gear of the first motor on the one hand, and with a second gear of the second shaft on the other hand.

The fact that the driving force for the rotational movement and the driving force for the translational movement of the medical instrument are transmitted to said medical instrument by both rollers at the same time makes it possible to improve efficiency in transmitting movement from the first motor and from the second motor. In addition, such a feature reduces the risk of slippage between the rollers and the medical instrument.

In addition, the fact that the motors are coupled to a shaft that transmits movement from the motor to the other shaft simplifies the structure of the drive system and improves the transmission.

In addition, the fact that the first shaft comprises a first gear that is meshed with an output gear of the first motor on the one hand, and with a second gear of the second shaft on the other hand, allows a compact and simple coupling, with high efficiency. The high efficiency arises in particular from the fact that the gears ensure an identical speed for the two rollers.

According to one advantageous feature, the first gear of the first shaft is rotationally integral with the first shaft while being translationally movable along said first shaft, and the second gear of the second shaft is rotationally integral with the second shaft while being translationally movable along said second shaft.

Such a feature allows decoupling the transmission of rotational movement from the first motor to the first and second shafts, from the translational movements of said first and second shafts, so that the first motor is not made to follow the translational movements or the second motor is not made to follow the rotational movements.

According to one advantageous feature, the first shaft comprises a third gear which is meshed on the one hand with an output gear of the second motor, and on the other hand with a fourth gear of the second shaft, the third gear of the first shaft comprising an internal thread which cooperates with an external thread formed on the first shaft in order to form a helical connection, and the fourth gear of the second shaft comprising an internal thread which cooperates with an external thread formed on the second shaft in order to form a helical connection.

Such a feature allows a compact and simple coupling, with high efficiency.

According to one advantageous feature, the second shaft comprises a fourth gear which is meshed on the one hand with an output gear of the second motor, and on the other hand with a third gear of the first shaft, the third gear of the first shaft comprising an internal thread which cooperates with an external thread formed on the first shaft in order to form a helical connection, and the fourth gear of the second shaft comprising an internal thread which cooperates with an external thread formed on the second shaft in order to form a helical connection.

Such a feature allows a compact and simple coupling, with high efficiency.

According to one advantageous feature, at least one among the first roller and the second roller is movable between a close position where the first roller and the second roller are spaced apart by a first spacing, and a distanced position where the first roller and the second roller are spaced apart by a second spacing, the first spacing being less than the second spacing, and a roller spacing device controls the position of the at least one among the first roller and the second roller, between its close position and its distanced position.

Such a feature makes it easier to install the medical instrument between the rollers and to remove it.

According to one advantageous feature, the first gear of the first shaft remains meshed with the second gear of the second shaft when the at least one among the first roller and the second roller is in its distanced position.

Such a feature allows simplifying the structure of the drive system and making it more compact, since it allows eliminating a device to manage the synchronization of the gears when they need to be re-engaged in cases where the gears are moved apart.

According to one advantageous feature, the roller spacing device comprises a third motor which rotates an eccentric ring fixed to the first shaft and/or to the second shaft, the center of said eccentric ring being offset relative to the first shaft or to the second shaft.

Such a feature is a simple, compact, and high-efficiency solution for controlling the spacing of the rollers.

According to one advantageous feature, a first toothed eccentric ring is fixed to the first shaft and forms a fifth gear which is meshed on the one hand with an output gear of the third motor, and on the other hand with a sixth gear of the second shaft formed by a second toothed eccentric ring; or a second toothed eccentric ring is fixed to the second shaft and forms a sixth gear which is meshed on the one hand with an output gear of the third motor, and on the other hand with a fifth gear of the first shaft formed by a first toothed eccentric ring.

Such a feature allows simplifying the structure of the roller spacing device and improving transmission.

According to another object, the invention proposes a catheter robot comprising a drive system for driving an elongate and flexible medical instrument along a main elongation axis, according to any one of the preceding features.

According to one advantageous feature, the catheter robot comprises:

- a support comprising a longitudinal axis;
- a first module comprising a first drive system for driving a first elongate and flexible medical instrument along the longitudinal axis according to any one of the preceding features;
- a second module comprising a second drive system for driving a second elongate and flexible medical instrument along the longitudinal axis according to any one of the preceding features; the first module being intended to be arranged between the patient and the second module, the second module being movable in longitudinal translation relative to the first module, the second module also comprising a rotation system for the first medical instrument which is controlled by the rotation of said first medical instrument via the first drive system.

Such a feature makes it possible to obtain a robot which is capable of manipulating two coaxial medical instruments by controlling both their rotational movements and their translational movements. In addition, the rotation system for the first medical instrument installed on the second module makes it possible to limit the torsion in said first medical instrument, such torsion possibly being created in particular by braking forces applied by a hemostasis valve installed at the proximal end of the first medical instrument.

According to one advantageous feature, the second module does not comprise any other system capable of driving a movement of the first medical instrument.

Such a feature allows simplifying the structure of the robot and reducing its size.

According to one advantageous feature, a third module comprises a third drive system for driving a third elongate and flexible medical instrument along the longitudinal axis according to any one of the preceding features, the second module being arranged between the first module and the third module, the third module being movable translationally relative to the second module, the third module also comprising a rotation system for the second medical instrument which is controlled by the rotation of said second medical instrument via the second drive system.

Such a feature makes it possible to manipulate three coaxial medical instruments while controlling both their rotational movements and their translational movements. In addition, the rotation system for the second medical instrument installed on the third module makes it possible to limit the torsion in said second medical instrument, such torsion possibly being created in particular by braking forces applied by a hemostasis valve installed at the proximal end of the second medical instrument.

According to one advantageous feature, the third module does not comprise any other system capable of driving a movement of the second medical instrument.

Such a feature allows simplifying the structure of the robot and reducing its size.

According to one advantageous feature, the first module comprises a first position-maintaining device for the first medical instrument, and/or the second module comprises a second position-maintaining device for the second medical instrument.

Such a feature allows ensuring that the first medical instrument and/or the second medical instrument remains stationary, in particular when the rollers of the drive systems are moving apart.

According to one advantageous feature, the third module comprises a third position-maintaining device for the third medical instrument.

Such a feature allows ensuring that the third medical instrument remains stationary, in particular when the rollers of the third drive system are moving apart.

According to one advantageous feature, the first position-maintaining device for the first medical instrument is located at a distance of less than or equal to 5 cm from the rollers of the first drive system, and/or the second position-maintaining device for the second medical instrument is located at a distance of less than or equal to 5 cm from the rollers of the second drive system.

Such a feature allows limiting the springback of the first medical instrument and/or second medical instrument when the rollers of the drive systems are moving apart.

According to one advantageous feature, the third position-maintaining device for the third medical instrument is located at a distance of less than or equal to 5 cm from the rollers of the third drive system.

Such a feature allows limiting the springback of the third medical instrument when the rollers of the third drive system are moving apart.

According to one advantageous feature, the rotation system for the first medical instrument of the second module comprises a pair of pads, the rotation system being configured to rotate the first medical instrument by gripping the first medical instrument with the pair of pads and moving the pads in opposite directions translationally along a direction perpendicular to the first medical instrument.

Such a feature makes it possible to manipulate the first medical instrument for all existing reference systems.

According to one advantageous feature, the rotation system for the second medical instrument of the third module comprises a pair of pads, the system being configured to rotate the second medical instrument by gripping the second medical instrument with the pair of pads and moving the pads in opposite directions translationally along a direction perpendicular to the second medical instrument.

Such a feature makes it possible to manipulate the second medical instrument for all existing reference systems.

According to one advantageous feature, the rotation system for the first medical instrument of the second module comprises an output gear which is configured to mesh with a gear located on the first medical instrument.

Such a feature allows simplifying the rotation system for the first instrument.

According to one advantageous feature, the rotation system for the second medical instrument of the third module comprises an output gear which is configured to mesh with a gear located on the second medical instrument.

Such a feature allows simplifying the rotation system for the second instrument.

Other features and advantages of the invention will become apparent upon reading the following description of a preferred embodiment of the invention, given by way of example and with reference to the appended drawings.

DETAILED DESCRIPTION

Throughout the remainder of the description text, and for all the figures, the terms catheter robot, medical robot, and medical catheter robot will be used interchangeably. The longitudinal axis of catheter robot 1 is the axis common to the elongate flexible medical instruments manipulated by catheter robot 1 and which corresponds to their main elongation axis. Furthermore, for simplification, rotation of the medical instrument will be used to refer to rotation of said medical instrument about its main elongation axis, and translation of the medical instrument will be used to refer to translation of said medical instrument along its main elongation axis.

Figure 1:
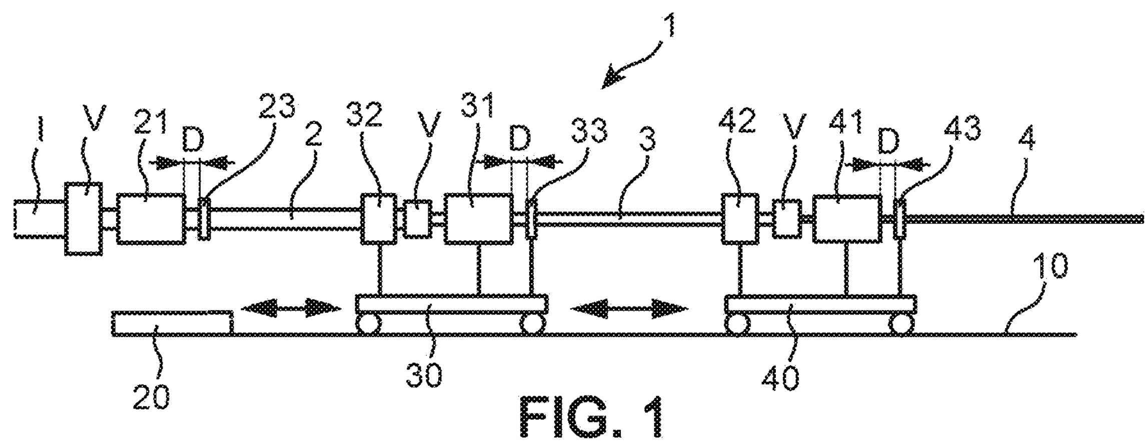
FIG. 1 schematically represents an example of a catheter robot for driving elongate flexible medical instruments according to one possible embodiment.

FIG. 1 schematically represents an example of a catheter robot 1 for driving elongate flexible medical instruments, according to one possible embodiment.

Catheter robot 1 comprises a support 10 on which are installed three modules for manipulating three elongate flexible medical instruments. Thus, catheter robot 1 comprises:

- a first module 20 which comprises a first drive system 21 for driving a first elongate flexible medical instrument 2 along the longitudinal axis of catheter robot 1, first drive system 21 being configured to drive first medical instrument 2 rotationally about the main axis and translationally along said main axis;
- a second module 30 which comprises a second drive system 31 for driving a second elongate flexible medical instrument 3 along the longitudinal axis of catheter robot 1, second drive system 31 being configured to drive second medical instrument 3 rotationally about the main axis and translationally along said main axis;
- a third module 40 which comprises a third drive system 41 for driving a third elongate flexible medical instrument 4 along the longitudinal axis of catheter robot 1, third drive system 41 being configured to drive third medical instrument 4 rotationally about the main axis and translationally along said main axis.

Second module 30 and third module 40 are both translationally movable along the main axis relative to support 10 of catheter robot 1, as well as relative to first module 20 which is fixed relative to support 10. In addition, third module 40 is translationally movable relative to second module 30, thus enabling second module 30 and third module 40 to have decoupled translational movements.

The translational mobility of second module 30 and third module 40 makes it possible to adapt the position of second module 30 and third module 40 according to the insertion of first medical instrument 20 and third medical instrument 30 into the patient's body. Thus, the position of second module 30 along support 10 is controlled by the translational movement of first medical instrument 2 via first drive system 21 of first module 20. Similarly, the position of third module 40 along support 10 is controlled by the translational movement of second medical instrument 3 via second drive system 31 of second module 30.

The translational movement of second module 30 and third module 40 along support 10 may for example be achieved with a system of rails forming slides along which second module 30 and third module 40 move.

According to one possible variant for using catheter robot 1, first medical instrument 2 is a guide catheter that enters the body of a patient via an introducer I. Second medical instrument 3 is a catheter or a microcatheter. Third medical instrument 4 is a guide wire.

Hemostasis valves V are installed at the following locations:

- at the proximal end of introducer I (i.e. the end directed towards the practitioner, opposite the patient);
- at the proximal end of first medical instrument 2;
- at the proximal end of second medical instrument 3.

As illustrated in FIG. 1, second module 30 comprises a rotation system 32 for rotating first medical instrument 2 about its main elongation axis. Rotation system 32 for first medical instrument 2 is controlled by the rotation of first medical instrument 2 via first drive system 21 of first module 20. Rotation system 32 for first medical instrument 2 installed on second module 30 thus ensures that the proximal end of first medical instrument 2 follows the same rotation as the part driven by first drive system 21, thus reducing the risk of torsion in first medical instrument 2. Indeed, hemostasis valve V installed at the proximal end of first medical instrument 2 generates friction that opposes the rotation of first medical instrument 2.

Similarly, third module 400 comprises a rotation system 42 for rotating second medical instrument 3 about its main elongation axis. Rotation system 42 for second medical instrument 3 is controlled by the rotation of second medical instrument 3 via second drive system 31 of second module 30. Rotation system 42 for second medical instrument 3 installed on third module 40 thus ensures that the proximal end of second medical instrument 3 follows the same rotation as the part driven by second drive system 31, thus reducing the risk of torsion in second medical instrument 3. Indeed, hemostasis valve V installed at the proximal end of second medical instrument 3 generates friction which opposes the rotation of second medical instrument 3.

First module 20 also comprises a first position-maintaining device 23 for first medical instrument 2. First position-maintaining device 23 for first medical instrument 2 is movable between a locking position where first position-maintaining device 23 grips first medical instrument 2 and prevents it from moving, and an open position where first position-maintaining device 23 leaves first medical instrument 2 free. First position-maintaining device 23 may for example be formed by a clamp.

Similarly, second module 30 also comprises a second position-maintaining device 33 for second medical instrument 3. Second position-maintaining device 33 for second medical instrument 3 is movable between a locking position where second position-maintaining device 33 grips second medical instrument 3 and prevents it from moving, and an open position where said second position-maintaining device 33 leaves second medical instrument 3 free. Second position-maintaining device 3 may for example be formed by a clamp.

Similarly, third module 40 also comprises a third position-maintaining device 43 for third medical instrument 4. Third position-maintaining device 43 for third medical instrument 4 is movable between a locking position where third position-maintaining device 43 grips third medical instrument 4 and prevents it from moving, and an open position where third position-maintaining device 43 leaves third medical instrument 4 free. Third position-maintaining device 4 may for example be formed by a clamp.

According to one advantageous feature, first position-holding device 23, second position-holding device 33, and third position-holding device 43 are located at a distance D that is less than or equal to 5 cm from the rollers of first drive system 21, second drive system 31, and third drive system 41 respectively. Such a distance D allows limiting the springback effect of the medical instrument when the drive system releases said medical instrument.

Figure 2:
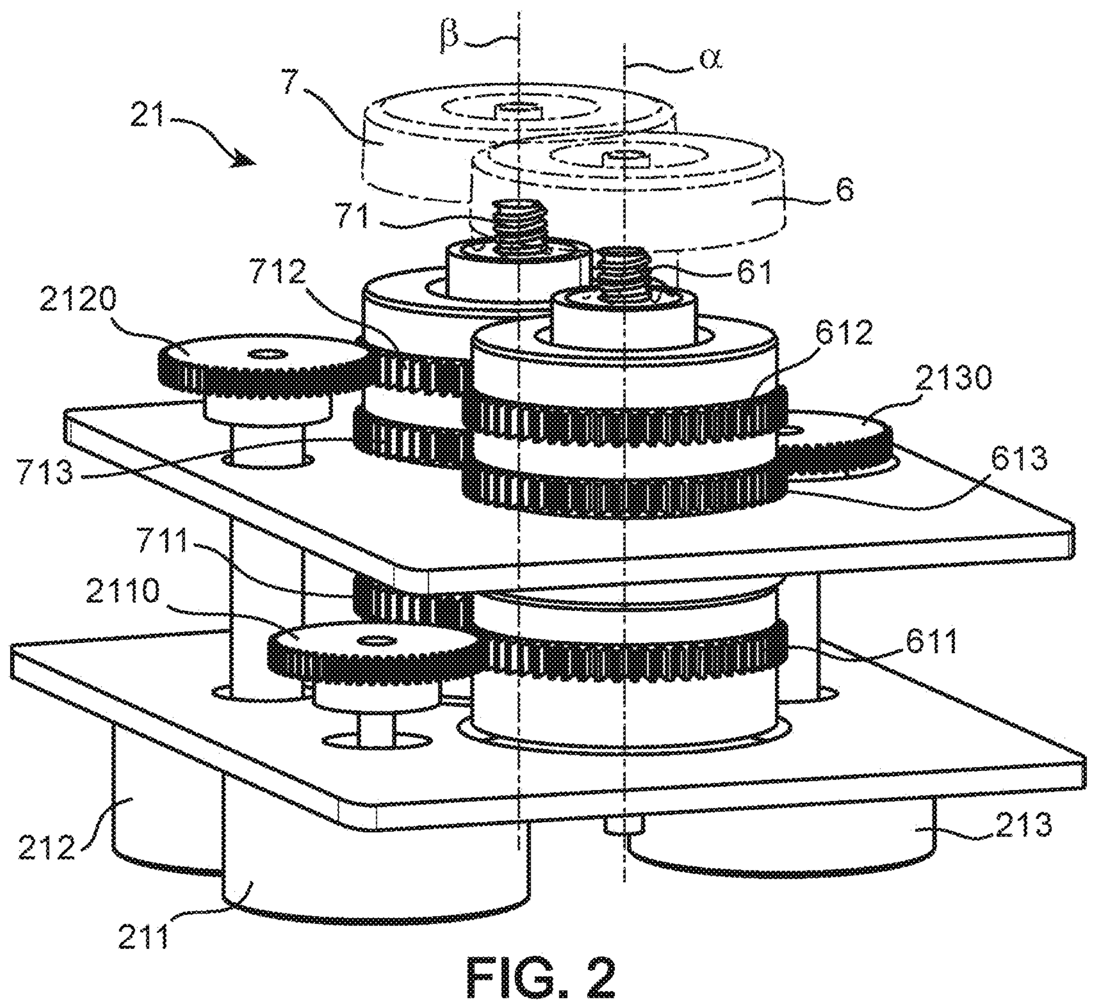
FIG. 2 schematically represents a drive system for driving an elongate flexible medical instrument according to one possible embodiment.
Figure 3:
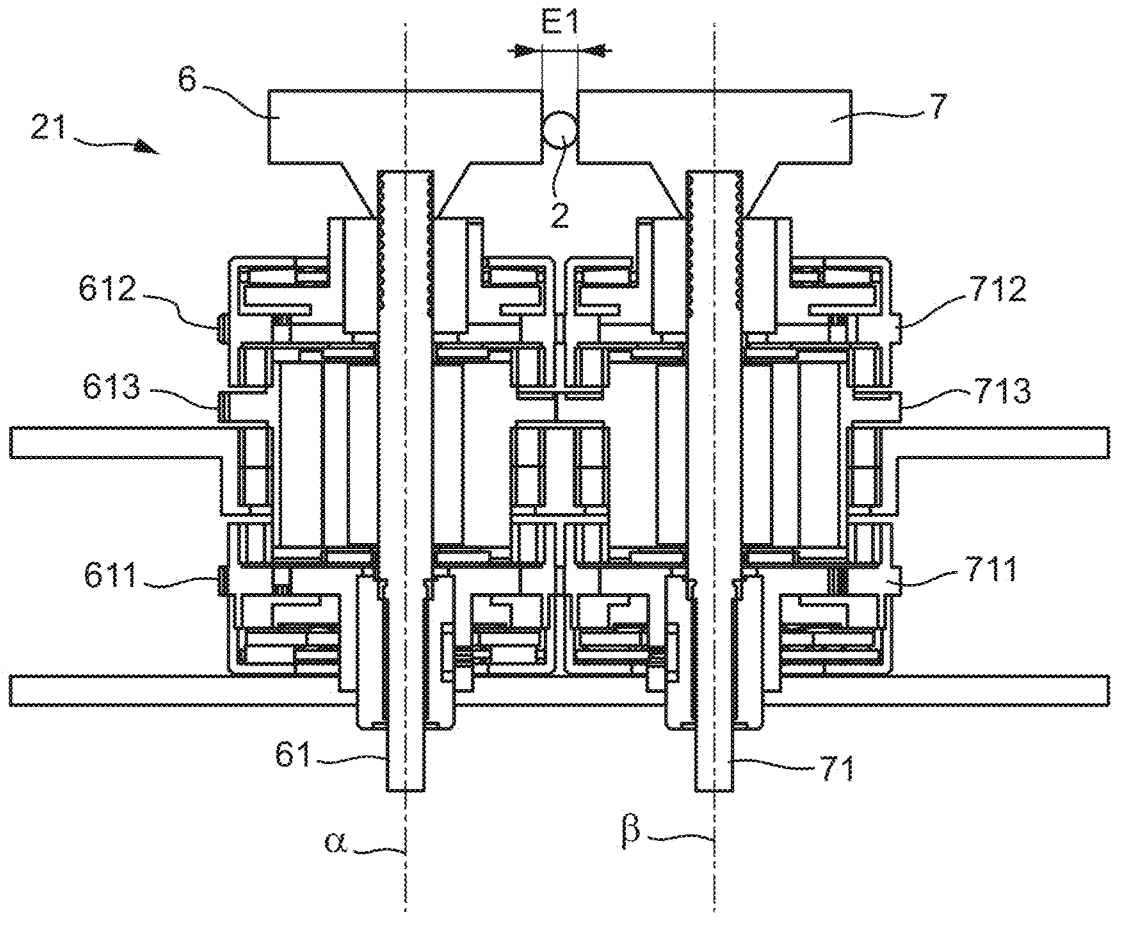
FIG. 3 schematically represents a section view of the drive system of FIG. 2 where the rollers are in a close position.
Figure 4:
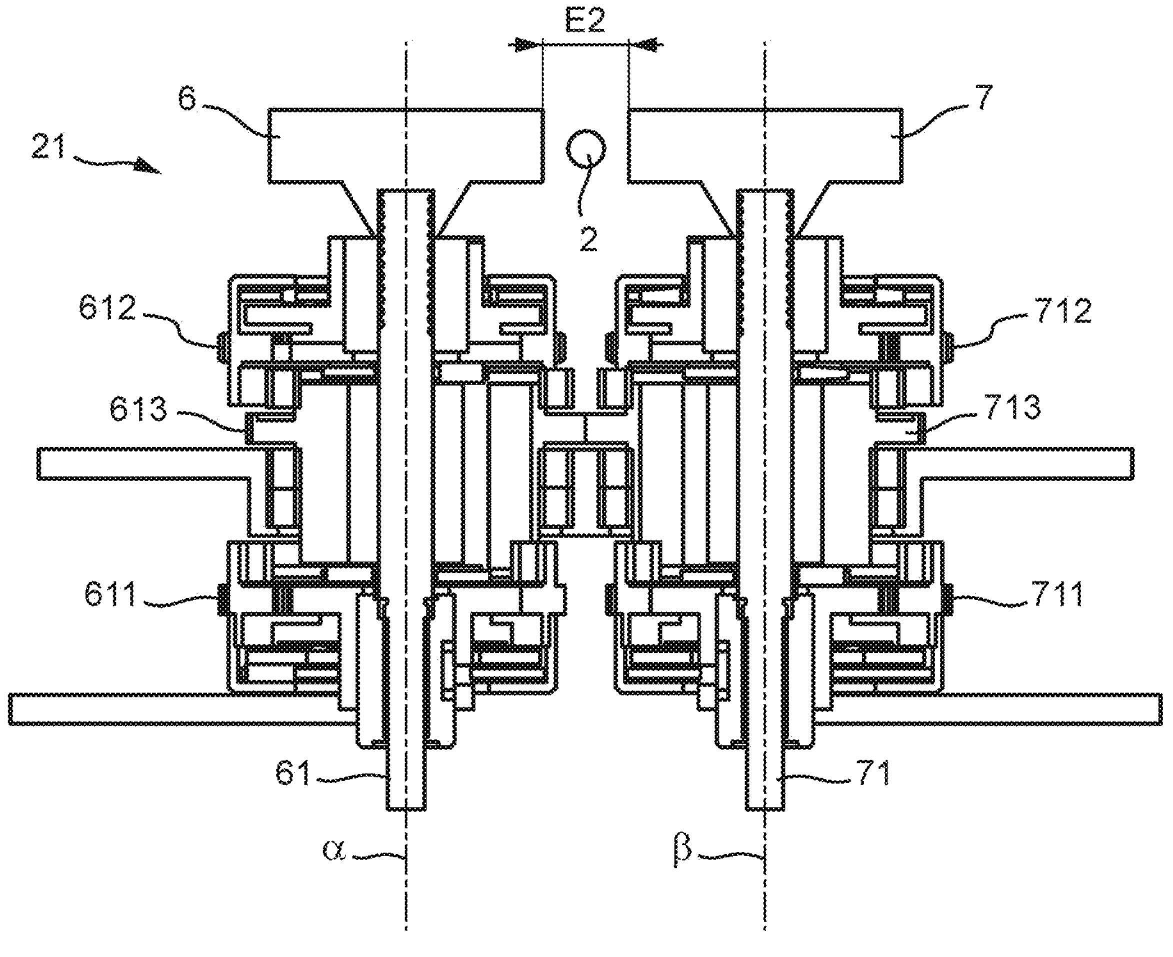
FIG. 4 schematically represents a section view of the drive system of FIG. 2 where the rollers are in a distanced position.

In order to simplify the structure of catheter robot 1, the first drive system 21 of first module 20, second drive system 31 of second module 30, and third drive system 41 of third module 40 are identical. In FIGS. 2, 3 and 4 reference is made to first drive system 21; however, FIGS. 2-4 also clearly illustrate second drive system 31 as well as third drive system 41.

As illustrated in FIGS. 2 to 4, first drive system 21 comprises:

- a first roller 6 coupled to a first shaft 61 which is perpendicular to the main axis of catheter robot 1, and
- a second roller 7 coupled to a second shaft 71 which is perpendicular to the main axis of catheter robot 1 and which is parallel to first shaft 61.

First roller 6 is rotatable about a first axis α which is collinear with first shaft 61, while second roller 7 is rotatable about a second axis β which is collinear with second shaft 71. Furthermore, first roller 6 is movable translationally along first axis α, and second roller 7 is movable translationally along second axis β.

First roller 6 and second roller 7 are configured to cooperate by gripping first medical instrument 2 between them and thus driving said first medical instrument 2 translationally and rotationally.

The translational movement of first medical instrument 2 is obtained on the one hand by rotation of first roller 6 about first axis α in a first direction, and on the other hand by rotation of second roller 7 about second axis β in a second direction which is opposite to the first direction.

The rotational movement of first medical instrument 2 is obtained on the one hand by translation of first roller 6 about first axis α in a first direction, and on the other hand by translation of second roller 7 along second axis β in a second direction which is opposite to the first direction.

First roller 6 and second roller 7 are capable of simultaneously performing a rotational movement and a translational movement in order to drive first medical instrument 2 in a combined rotational and translational movement.

First roller 6 and second roller 7 may for example each be formed by a cylinder of revolution, made of elastomer.

First drive system 21 also comprises:

- a first motor 211 which is intended to drive first roller 6 and second roller 7 rotationally;
- second motor 212 which is intended to drive first roller 6 and second roller 7 translationally;
- a third motor 213 which is intended to move first roller 6 and second roller 7 further apart or closer together.

In order to transmit rotational movement to first roller 6 and second roller 7, first motor 211 is coupled to first shaft 61, first shaft 61 itself being coupled to second shaft 71 so as to transmit thereto the rotational movement from first motor 211. Thus, first medical instrument 2 is driven translationally by a driving force coming from both first roller 6 and second roller 7.

Preferably, the coupling between first motor 211, first shaft 61, and second shaft 71 is carried out with gears. Thus, first motor 211 comprises an output gear 2110 which is meshed with a first gear 611 located on first shaft 61, first gear 611 also being meshed with a second gear 711 located on second shaft 71.

In order to allow the coupling between first motor 211, first gear 611, and second gear 711, while allowing the translation of first shaft 61 and second shaft 71, first gear 611 is mounted on first shaft 61 so as to be free to move translationally along first shaft 61 but is integral with first shaft 61 for all other movements, and second gear 711 is mounted on second shaft 71 so as to be free to move translationally along second shaft 71 but is integral with second shaft 71 for all other movements. A stop may be installed on first shaft 61 and on second shaft 71 in order to limit the amplitude of the translational movement of first gear 611 and second gear 711 along first shaft 61 and second shaft 71 respectively.

In order to transmit translational movement to first roller 6 and second roller 7, second motor 212 is coupled to second shaft 71, second shaft 71 itself being coupled to first shaft 61 so as to transmit thereto the movement from second motor 212. Thus, first medical instrument 2 is rotated by a driving force coming from both first roller 6 and second roller 7.

According to another possible variant, second motor 212 is coupled to first shaft 61, first shaft 61 itself being coupled to second shaft 71 in order to transmit thereto the driving force from second motor 212.

Preferably, the coupling between second motor 212, first shaft 61, and second shaft 71 is done with gears. Thus, as illustrated in the variant of FIGS. 2-4, second motor 212 comprises an output gear 2120 which is meshed with a fourth gear 712 located on second shaft 71, said fourth gear 712 also being meshed with a third gear 612 located on first shaft 61. According to another variant not shown in the figures, output gear 2120 of second motor 212 is meshed with third gear 612 of first shaft 61, third gear 612 also being meshed with fourth gear 712 of second shaft 71.

In order to convert the rotational movement coming from second motor 212 into a translational movement of first shaft 61, third gear 612 comprises an internal thread which cooperates with an external thread formed on first shaft 61 to thus form a helical connection. Similarly, in order to convert the rotational movement coming from second motor 212 into a translational movement of second shaft 71, fourth gear 712 comprises an internal thread which cooperates with an external thread formed on second shaft 71 to thus form a helical connection. If the user wishes to drive first medical instrument 2 translationally only, catheter robot 1 activates both first motor 211 and second motor 212 so that first roller 6 and second roller 7 rotate in opposite directions without translational movement. Activation of first motor 211 causes rotation of first shaft 61 and second shaft 71. The fact that first shaft 61 and second shaft 71 are rotating tends to cause them to move translationally by screwing them respectively into the internal thread of third gear 612 and of fourth gear 712. To counter this phenomenon and maintain only the rotational movement of first shaft 61 and second shaft 71, activation of the second motor 212 allows rotating third gear 612 and fourth gear 712 at the same speed and in the same direction as first shaft 61 and second shaft 71 respectively, thus preventing a screwing advancement of first shaft 61 and second shaft 71.

If the user wishes to drive first medical instrument 2 rotationally only, catheter robot 1 activates only second motor 212 so that first roller 6 and second roller 7 move translationally in opposite directions, without rotating. Activation of second motor 212 causes rotation of third gear 612 and fourth gear 712. Rotation of third gear 612 and fourth gear 712 allows first shaft 61 and second shaft 71 to be screwed respectively into the internal thread of third gear 612 and fourth gear 712, thereby driving the translational movement of first shaft 61 and second shaft 71.

If the user wishes to drive first medical instrument 2 both rotationally and translationally, catheter robot 1 activates both first motor 211 and second motor 212 so that first roller 6 and second roller 7 move translationally in opposite directions while also rotating in opposite directions. As indicated above, the activation of first motor 211 causes the rotation of first shaft 61 and second shaft 71. Furthermore, the activation of second motor 212 allows controlling the screwing advancement of first shaft 61 and second shaft 71 respectively into internal threads of third gear 612 and fourth gear 712, thus controlling the translational movement of first shaft 61 and second shaft 71.

In order to move first roller 6 and second roller 7 further apart or closer together, third motor 213 is coupled to first shaft 61, first shaft 61 itself being coupled to second shaft 71 in order to transmit thereto the driving force coming from third motor 213.

Preferably, the coupling between third motor 213, first shaft 61, and second shaft 71 is done with gears. Thus, third motor 213 comprises an output gear 2130 which is meshed with a fifth gear 613 located on first shaft 61, said fifth gear 613 also being meshed with a sixth gear 713 located on second shaft 71. According to another possible variant, output gear 2130 is meshed with sixth gear 713 located on second shaft 71, sixth gear 713 also being meshed with fifth gear 613 located on first shaft 61.

In the variant illustrated in FIGS. 2-4, first roller 6 and second roller 7 are both movable between a close position where first roller 6 and second roller 7 are spaced apart by a first spacing E1, and a distanced position where first roller 6 and second roller 7 are spaced apart by a second spacing E2, first spacing E1 being less than second spacing E2.

The close position is illustrated in FIG. 3 and corresponds to a working position where first roller 6 and the second roller grip first medical instrument 2 in order to manipulate it.

The distanced position is illustrated in FIG. 4 and corresponds to a release position where first medical instrument 2 is no longer in contact with at least one among first roller 6 and second roller 7, thus allowing the installation or removal of first medical instrument 2.

According to one possible variant, only first roller 6 is movable between the distanced position and the close position, second roller 7 remaining stationary. According to another possible variant, only second roller 7 is movable between the distanced position and the close position, first roller 6 remaining stationary.

In the embodiment illustrated in FIGS. 2 to 4, the movement of first roller 6 and second roller 7 away from or towards each other is obtained because fifth gear 613 and sixth gear 713 are eccentric gears. The center of fifth gear 613 is offset relative to first shaft 61, and the center of sixth gear 713 is offset relative to second shaft 71.

Because fifth gear 613 has rotation about first shaft 61 as its only degree of freedom, rotation of fifth gear 613 causes rotation of first shaft 61 about the center of fifth gear 613, and therefore the radial offset of first shaft 61 and first roller 6 relative to second shaft 71 and second roller 7.

Similarly, because sixth gear 713 has rotation about second shaft 71 as its only degree of freedom, rotation of sixth gear 713 causes rotation of second shaft 71 about the center of sixth gear 713, and therefore the radial offset of second shaft 71 and second roller 7 relative to first shaft 61 and first roller 6.

According to a preferred variant which allows simplifying the structure of robot catheter 1 and reducing its size, rotation system 32 for second module 30 and rotation system 42 for third module 40 are respectively capable of driving first medical instrument 2 and second medical instrument 3 rotationally only. Rotation system 32 for second module 30 and rotation system 42 for third module 40 are thus not respectively capable of driving first medical instrument 2 and second medical instrument 3 translationally.

Furthermore, preferably, second module 30 does not comprise any other system for driving movement of first medical instrument 2 other than rotation system 32. Similarly, third module 40 also does not comprise any other system for driving movement of second medical instrument 3 other than rotation system 42.

Figure 5:
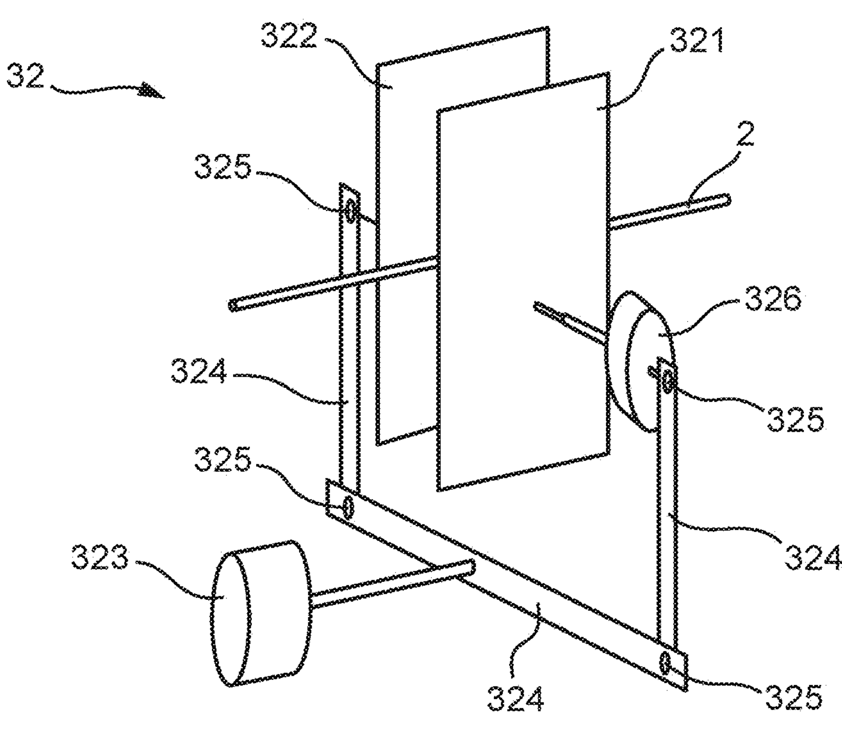
FIG. 5 schematically represents a system for rotation only of an elongate flexible medical instrument according to a first possible variant.
Figure 6:
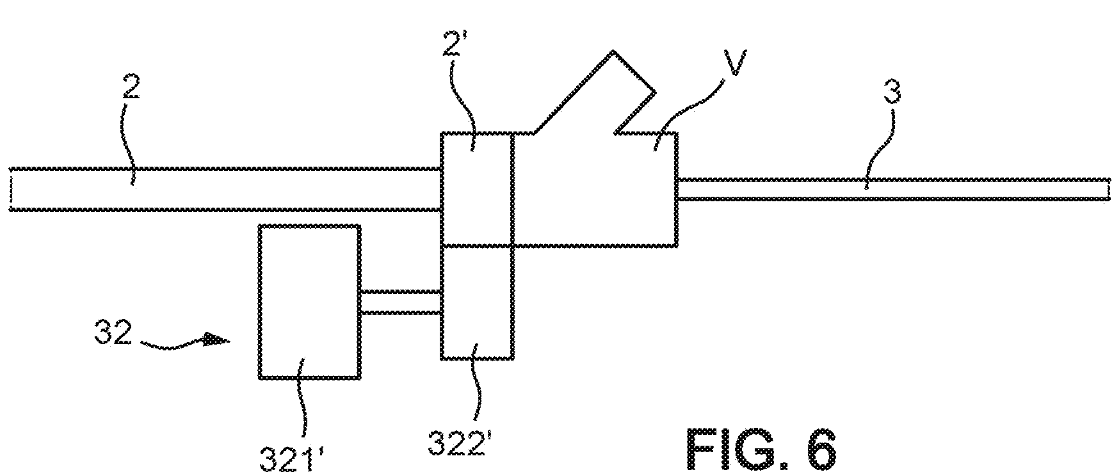
FIG. 6 schematically represents a system for rotation only of an elongate flexible medical instrument according to a second possible variant.
Figure 7:
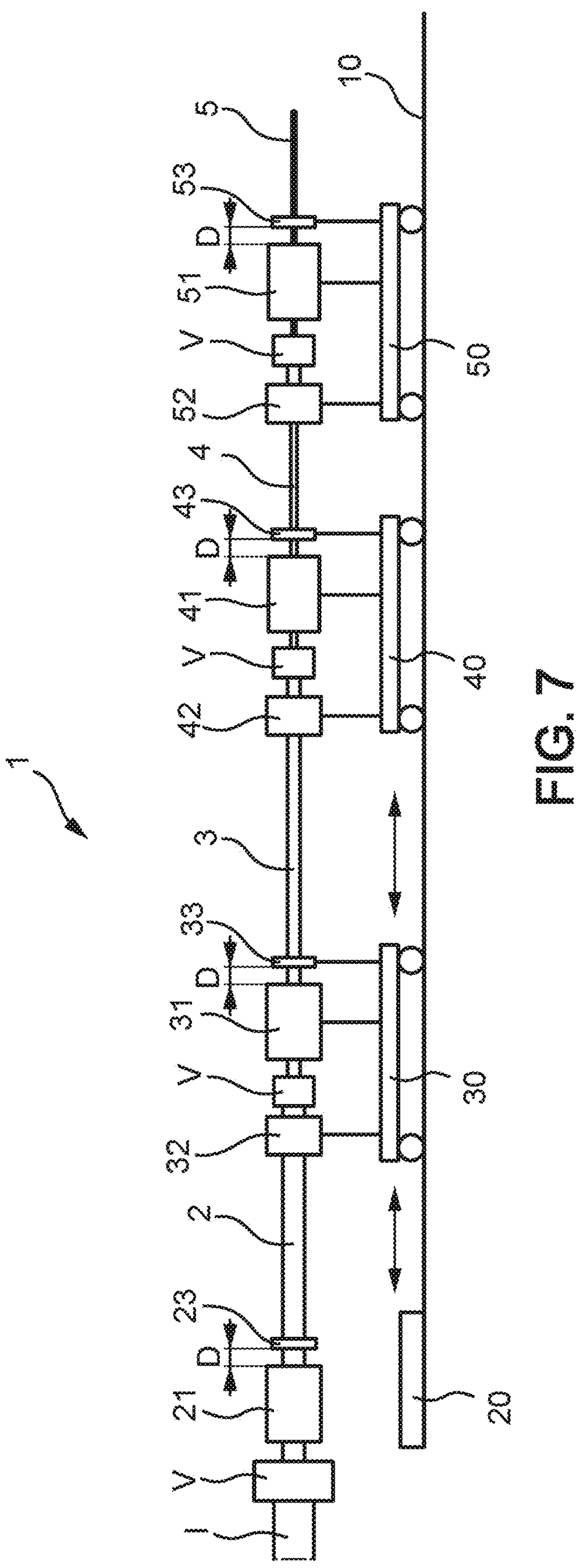
FIG. 7 schematically represents a variant of a catheter robot for driving four elongate flexible medical instruments.

In order to simplify the structure of catheter robot 1, rotation system 32 for second module 30 and rotation system 42 for third module 40 are identical. In FIGS. 5 and 6, reference is made to rotation system 32 for second module 30; however, FIGS. 5 and 6 also illustrate rotation system 42 for third module 40. Furthermore, in the case where catheter robot 1 comprises a fourth module 50 with rotation system 52, rotation system 52 for fourth module 50 is also identical to rotation system 32 for second module 30.

According to a first variant illustrated in FIG. 5, rotation system 32 comprises a first pad 321 and a second pad 322 located opposite said first pad 321 so as to be one on either side of first medical instrument 2. Rotation system 32 is configured to rotate first medical instrument 2 on the one hand by gripping first medical instrument 2 between first pad 321 and second pad 322, and on the other hand by translationally moving first pad 321 and second pad 322 in a direction perpendicular to first medical instrument 2 and in opposite directions to each other. The translational movement of first pad 321 and second pad 322 is obtained by a rotary motor 323 whose rotational movement is converted to translational movement by an assembly of connecting rods 324 interconnected by pivots 325.

In order to allow first pad 321 and second pad 322 to grip or release first medical instrument 2, a linear motor 326 is installed so as to move first pad 321 closer to or further away from second pad 322. In this variant, only first pad 321 is movable for tightening and loosening, while second pad 322 remains fixed. According to another possible variant, both first pad 321 and second pad 322 are movable for tightening and loosening. Loosening the pair of pads allows the pads to perform their return movement during rotation of first medical instrument 2, and allows the installation or removal of first medical instrument 2.

According to a second variant illustrated in FIG. 6, rotation system 32 comprises a rotary motor 321' which rotates an output gear 322'. Output gear 322' is meshed with a gear 2' located on the proximal end of first medical instrument 2. Gear 2' may be an added part which is fixed on the proximal end of first medical instrument 2, or the proximal end of first medical instrument 2 may be manufactured so as to have teeth and thus form gear 2'.

Figure 8:
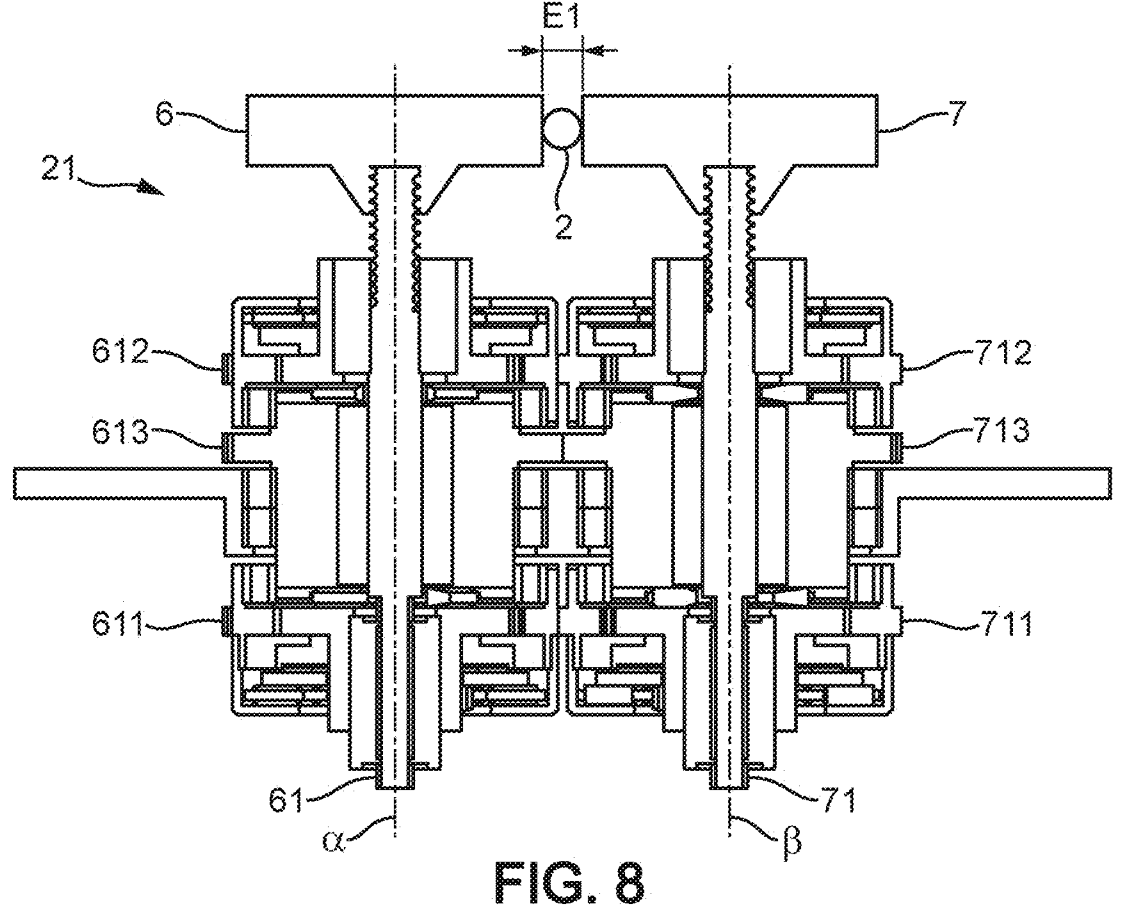
FIG. 8 schematically represents a section view of the drive system according to another embodiment where the rollers are in a close position.
Figure 9:
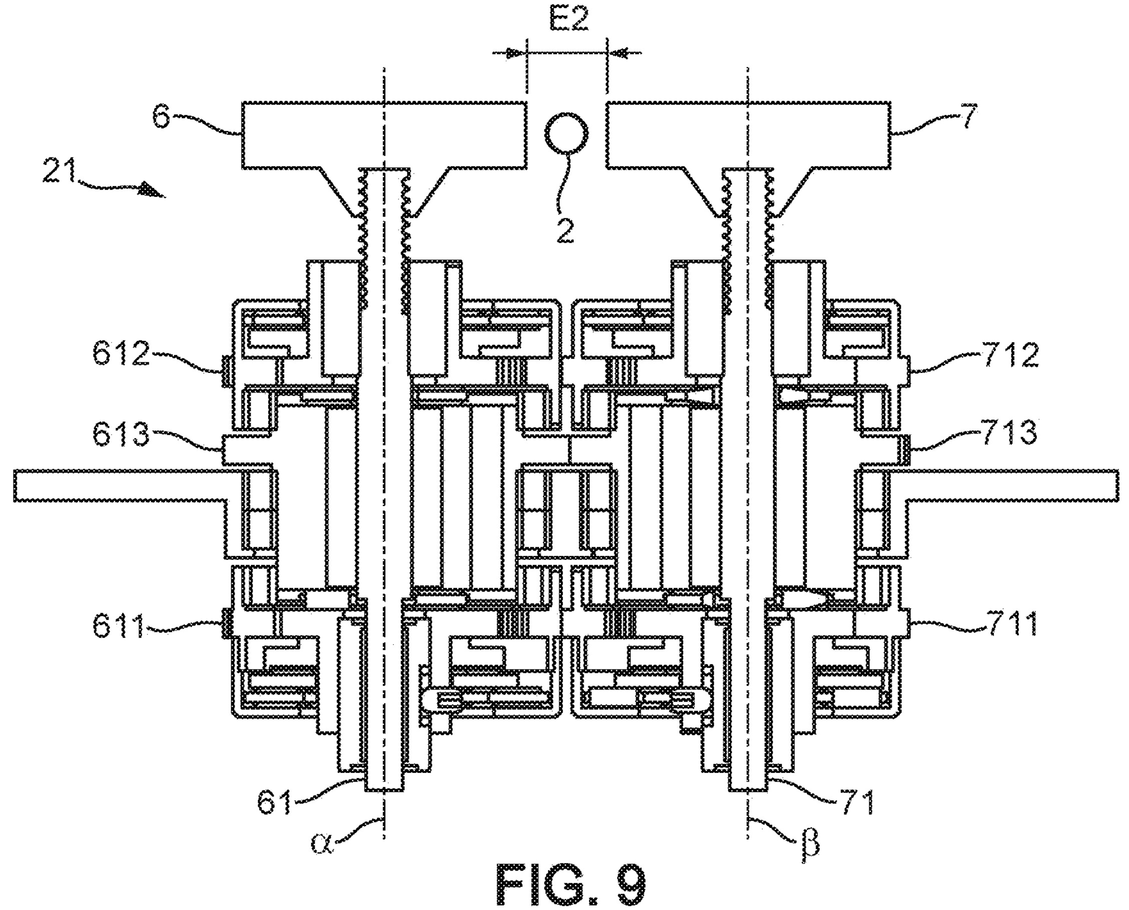
FIG. 9 schematically represents a section view of the drive system of FIG. 8 where the rollers are in a distanced position.

The embodiment illustrated in FIGS. 8 and 9 is similar to the one illustrated in FIGS. 3 and 4 and varies only in that first gear 611 remains meshed with second gear 711, and third gear 612 remains meshed with fourth gear 712, when rollers 6 and 7 are in the distanced position. The fact that the gears remain meshed makes it possible to avoid gear synchronization problems when the gears have been moved apart and must re-mesh, and thus allows not installing a device to ensure that the gears are rotating at the same speed as they re-mesh.

In the embodiment of FIGS. 8 and 9, the movement further apart or closer together of first roller 6 and second roller 7 is also obtained because fifth gear 613 and sixth gear 713 are eccentric gears. The center of fifth gear 613 is offset relative to first shaft 61, and the center of sixth gear 713 is offset relative to second shaft 71.

In the embodiment of FIGS. 8 and 9, first gear 611 remains meshed with second gear 711, and third gear 612 remains meshed with fourth gear 712, in all positions of rollers 6 and 7.

Of course, the invention is not limited to the examples and embodiments described and shown, but it capable of numerous variants accessible to those skilled in the art. For example, catheter robot 1 may comprise only two modules for manipulating two elongate flexible medical instruments, or catheter robot 1 may comprise more than three modules in order to manipulate more than three elongate flexible medical instruments.

The invention claimed is:

1. A drive system for driving an elongate and flexible medical instrument along a main elongation axis, said drive system comprising: a first roller and a second roller which are intended to cooperate in order to drive the medical instrument translationally along its main elongation axis, and to drive the medical instrument rotationally about its main elongation axis, the first roller being coupled to a first shaft and the second roller being coupled to a second shaft:

a first motor which is coupled to the first shaft, said first motor being configured to drive the first shaft and the first roller rotationally about a first axis that is collinear with the first shaft, the first shaft being coupled to the second shaft in order to transmit motion from the first motor to said second shaft and thus drive the second shaft and the second roller rotationally about a second axis that is collinear with the second shaft, the medical instrument being driven translationally by a driving force transmitted both by the rotation of the first roller and by the rotation of the second roller; and a second motor which is coupled to the first shaft, said second motor being configured to drive the first shaft and the first roller translationally along the first axis, the first shaft being coupled to the second shaft in order to transmit motion from the second motor to said second shaft and thus drive the second shaft and the second roller translationally along the second axis in the opposite direction relative to the first roller, the medical instrument being rotated by a driving force transmitted both by the translation of the first roller and by the translation of the second roller; or a second motor which is coupled to the second shaft, said second motor being configured to drive the second shaft and the second roller translationally along the second axis, the second shaft being coupled to the first shaft in order to transmit motion from the second motor to said first shaft and thus drive the first shaft and the first roller translationally along the first axis in the opposite direction relative to the second roller, the medical instrument being rotated by a driving force transmitted both by the translation of the first roller and by the translation of the second roller;

wherein the first shaft comprises a first gear which is meshed with an output gear of the first motor on the one hand, and with a second gear of the second shaft on the other hand.

2. The drive system according to claim 1, wherein the first gear of the first shaft is rotationally integral with the first shaft while being translationally movable along said first shaft; and the second gear of the second shaft is rotationally integral with the second shaft while being translationally movable along said second shaft.

3. The drive system according to claim 1, wherein the first shaft comprises a third gear which is meshed on the one hand with an output gear of the second motor, and on the other hand with a fourth gear of the second shaft, wherein the third gear of the first shaft comprises an internal thread which cooperates with an external thread formed on the first shaft in order to form a helical connection, and the fourth gear of the second shaft comprises an internal thread which cooperates with an external thread formed on the second shaft in order to form a helical connection.

4. The drive system according to claim 1, wherein the second shaft comprises a fourth gear which is meshed on the one hand with an output gear of the second motor, and on the other hand with a third gear of the first shaft, wherein the third gear of the first shaft comprises an internal thread which cooperates with an external thread formed on the first shaft in order to form a helical connection, and the fourth gear of the second shaft comprises an internal thread which cooperates with an external thread formed on the second shaft in order to form a helical connection.

5. The drive system according to claim 1, wherein at least one among the first roller and the second roller is movable between a close position where the first roller and second roller are spaced apart by a first spacing, and a distanced position where the first roller and the second roller are spaced apart by a second spacing, the first spacing being less than the second spacing; and a roller spacing device controls the position of the at least one among the first roller and the second roller, between its close position and its distanced position.

6. The drive system according to claim 5, wherein the first gear of the first shaft remains meshed with the second gear of the second shaft when the at least one among the first roller and the second roller is in its distanced position.

7. The drive system according to claim 5, wherein the roller spacing device comprises a third motor which rotates an eccentric ring fixed to the first shaft and/or to the second shaft, the center of said eccentric ring being offset relative to the first shaft or to the second shaft.

8. The drive system according to claim 7, wherein a first toothed eccentric ring is fixed to the first shaft and forms a fifth gear which is meshed on the one hand with an output gear of the third motor, and on the other hand with a sixth gear of the second shaft formed by a second toothed eccentric ring; or a second toothed eccentric ring is fixed to the second shaft and forms a sixth gear which is meshed on the one hand with an output gear of the third motor, and on the other hand with a fifth gear of the first shaft formed by a first toothed eccentric ring.

9. A catheter robot comprising a drive system for driving an elongate and flexible medical instrument along a main elongation axis, according to claim 1.

10. The catheter robot according to claim 9, comprising:

a support comprising a longitudinal axis;

a first module comprising a first drive system for driving a first elongate and flexible medical instrument along the longitudinal axis;

a second module comprising a second drive system for driving a second elongate and flexible medical instrument along the longitudinal axis;

the first module being intended to be arranged between the patient and the second module, the second module being movable in longitudinal translation relative to the first module, the second module also comprising a rotation system for the first medical instrument which is controlled by the rotation of said first medical instrument via the first drive system.

11. The catheter robot according to claim 10, wherein the second module does not comprise any other system capable of driving a movement of the first medical instrument.

12. The catheter robot according to claim 10, comprising a third module which comprises a third drive system for driving a third elongate flexible medical instrument along the longitudinal axis, the second module being arranged between the first module and the third module, the third module being movable translationally relative to the second module, the third module also comprising a rotation system for the second medical instrument which is controlled by the rotation of said second medical instrument via the second drive system.

13. The catheter robot according to claim 12, wherein the third module does not comprise any other system capable of driving a movement of the second medical instrument.

14. The catheter robot according to claim 12, wherein the rotation system for the second medical instrument of the third module comprises a pair of pads, the rotation system being configured to rotate the second medical instrument by gripping the second medical instrument with the pair of pads and moving the pads in opposite directions translationally along a direction perpendicular to the second medical instrument.

15. The catheter robot according to claim 12, wherein the rotation system for the second medical instrument of the third module comprises an output gear which is configured to mesh with a gear located on the second medical instrument.

16. The catheter robot according to claim 10, wherein the first module comprises a first position-maintaining device for the first medical instrument and/or the second module comprises a second position-maintaining device for the second medical instrument.

17. The catheter robot according to claim 16, wherein the third module comprises a third position-maintaining device for the third medical instrument.

18. The catheter robot according to claim 16, wherein the first position-maintaining device for the first medical instrument is located at a distance of less than or equal to 5 cm from the rollers of the first drive system, and/or the second position-maintaining device for the second medical instrument is located at a distance of less than or equal to 5 cm from the rollers of the second drive system.

19. The catheter robot according to claim 18, wherein the third position-maintaining device for the third medical instrument is located at a distance of less than or equal to 5 cm from the rollers of the third drive system.

20. The catheter robot according to claim 10, wherein the rotation system for the first medical instrument of the second module comprises a pair of pads, the rotation system being configured to rotate the first medical instrument by gripping the first medical instrument with the pair of pads and moving the pads in opposite directions translationally along a direction perpendicular to the first medical instrument.

21. The catheter robot according to claim 10, wherein the rotation system for the first medical instrument of the second module comprises an output gear which is configured to mesh with a gear located on the first medical instrument.

* * * * *